United States Patent [19]

Stout et al.

[11] Patent Number: 4,748,184

[45] Date of Patent: May 31, 1988

[54] ARYL SUBSTITUTED AMINOMETHYL BENZENE DERIVATIVES HAVING ANTIARRHYTHMIC UTILITY

[75] Inventors: David M. Stout; William L. Matier, both of Libertyville; Lawrence A. Black, Vernon Hills, all of Ill.

[73] Assignee: E. I. Du Pont de Nemours and Company, Wilmington, Del.

[21] Appl. No.: 813,734

[22] Filed: Dec. 27, 1985

Related U.S. Application Data

[63] Continuation-in-part of Ser. No. 401,751, Jul. 26, 1982, Pat. No. 4,562,201.

[51] Int. Cl.$^4$ .................. A61K 31/40; A61K 31/455; C07D 403/10; C07D 401/10
[52] U.S. Cl. ...................... 514/422; 548/524; 546/190; 540/596; 514/212; 514/316; 544/72; 560/42; 564/165; 564/223
[58] Field of Search ............... 548/524; 546/190; 514/316, 422, 212; 540/596

[56] References Cited

U.S. PATENT DOCUMENTS 3,285,912 11/1966 Palopoli et al. ............... 548/524
3,287,363 11/1966 Palopoli et al. ............... 548/524
4,305,940 12/1981 Quadro ........................ 548/578
4,323,691 4/1982 Ours et al. .................... 548/524
4,362,738 12/1982 Keck et al. ................... 548/494 X

OTHER PUBLICATIONS

Boucherle, Chimie Therapeutique (1967) No. 6, pp. 410–414.
Li, et al., Chemical Abstracts, vol. 92 (1980), Entry 121950t.
Sun, et al., Yao Hsueh Hsueh Pao., vol. 16(8) (1981), pp. 564–570.

Primary Examiner—Donald G. Daus
Assistant Examiner—William A. Teoli, Jr.
Attorney, Agent, or Firm—Gildo E. Fato

[57] ABSTRACT

The present invention relates to new compounds of the formula

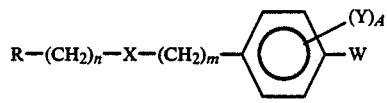

wherein X is

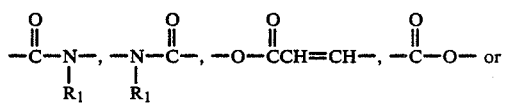

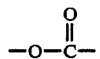

wherein $R_1$ is hydrogen, lower alkyl, phenyl, benzyl, cinnamoyl, thiophene, furan, pyrrole, imidazole, pyrazole oxazole or thiazole; W is hydrogen or hydroxy; $(Y)_A$ is positioned ortho to W and is an aminoloweralkyl having the formula —$CH_2NR_2R_3$ where $R_2$ and $R_3$ are the same or different and may be lower alkyl or $R_2$ and $R_3$ may together with N form a pyrrolidine, piperidine or azepine ring, and A is 2; n and m are independently from 0 to 5; and R is straight or branched $C_1$–$C_{10}$ alkyl, straight or branched $C_3$–$C_{10}$ cycloalkyl, straight or branched $C_2$–$C_4$ alkenyl or straight or branched $C_2$–$C_4$ alkynyl, or a pharmaceutically acceptable salt thereof.

These compounds are useful in the treatment of various cardiac arrhythmias.

19 Claims, No Drawings

ARYL SUBSTITUTED AMINOMETHYL BENZENE DERIVATIVES HAVING ANTIARRHYTHMIC UTILITY

This is a continuation-in-part of application Ser. No. 401,751, filed July 26, 1982 now U.S. Pat. No. 4,562,201.

BACKGROUND OF THE INVENTION

Cardiac arrhythmias represent a clinically significant disorder of the normal rhythm of the heart and usually require immediate and specific therapy. A common cause of cardiac arrhythmias is coronary artery disease, where a high incidence of arrhythmias has been observed during acute myocardial infarction. Premature ventricular contractions and sinus tachycardia are among the two most common types of arrhythmias associated with myocardial infarction. Although these and other types of arrhythmias can be suppressed by the use of antiarrhythmic agents, the prevention of the recurrence of tachyarrhythmias is often necessary for long periods of time or even indefinitely. Consequently, these antiarrhythmic drugs must not only be effective and reliable, but they must have a minimal number of adverse side-effects associated therewith.

The heart is endowed with a specialized excitatory system for generating rhythmical impulses that cause rhythmical contraction of the heart muscle and conductive system for conducting these impulses throughout the heart. A major portion of cardiac disorders is based on abnormalities of this specialized excitatory and conductive system resulting in irregular sinus rhythm. Cardiac arrhythmias as described above, and in particular tachyarrhythmias, are caused by disorders of electrical impulse formation, by disturbances in impulse conduction, or by a combination of the two. Drugs used to treat tachyarrhythmias generally reduce or suppress excitation of the heart muscle by depressing spontaneous diastolic depolarization, and affect conduction by altering the conduction velocity through the myocardial tissue and the duration of the refractory period.

Antiarrhythmic drugs are generally administered on a long-term basis to maintain normal sinus rhythm after electrical cardioversion after normal cardiac action has been restored as alluded to above. Quinidine, 6-methoxy-α-(5'-vinyl-2-quinuclidinyl)-4-quindinemethanol and disopyramide, α[2-(diisopropylamino)-ethyl-]α-phenol-2-pyridineacetamide are two antiarrhythmic agents which depress impulse formation, slow conduction velocity, and increase the duration of the refractory period of cardiac cells; and thus are useful in the treatment of supraventricular and ventricular tachyarrhythmias. However, in addition to the direct effect on the cardiac rhythm, both of these agents exhibit indirect anticholinergic actions which may affect the vagal stimulation of the heart and have an affect on peripheral parasympathetic stimulation.

Both quinidine and disopyramide exhibit adverse side-effects when administered to patients for the management of arrhythmias. The side-effects associated with quinidine include, inter alia, cardiotoxicity, diarrhea, nausea, vomiting, fever, hypertension and depression of myocardial contractility. Likewise, the side effects associated with associated with disopyramide include, inter alia, dryness of the mouth, blurred vision, constipation, and urinary retention, and depression of myocardial contractility.

Changrolin, 4-[3',5'-bis[N-pyrolidinylmethyl]-4'-hydroxyanilino]quinazoline, an effective antiarrhythmic agent, also possesses substantial anticholinergic activity together with the ability to cause skin discoloration in some patients.

Heretofore, there has not been an effective antiarrhythmic agent available that has not been plagued by one or more of these unwanted, adverse side-effects, many of which are caused by excessive anticholinergic activity. In accordance with the present invention, disclosed are compounds having effective antiarrhythmic activity with less of the unwanted anticholinergic activity associated with these antiarrhythmic drugs.

SUMMARY OF THE INVENTION

In accordance with the present invention, disclosed herein are compounds of the formula

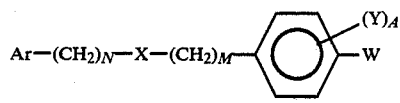

wherein x is

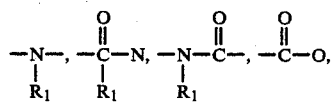

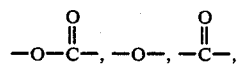

lower straight chained alkylene, or —S— wherein $R_1$ is hydrogen, aryl, or lower alkyl; W is hydrogen, hydroxy, amino,

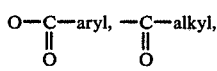

—O—alkyl, alkylsulfonamido or —O—aralkyl; $(Y)_A$ is positioned ortho to W and is an aminoalkyl having the formula —$CH_2NR_2R_3$, wherein $R_2$ and $R_3$ may together with N form a 5- to 7-membered heterocyclic group optionally including oxygen, nitrogen, or sulfur as a second heteroatom, and A is 1 or 2 with the proviso that when A is 1 that W is hydroxy, amino,

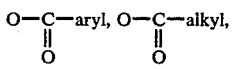

—O—alkyl, or —O—aralkyl; N and M are independently from 0 to about 5; and Ar is a substituted or unsubstituted aryl and is phenyl, a 5-membered heterocyclic group having sulfur, oxygen, or nitrogen as a heteroatom, or a 7-membered heterocyclic group having nitrogen as a heteroatom, each of which is optionally fused with one or more aromatic groups, with the proviso that when Ar is phenyl that it is represented by the formula

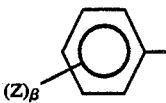

wherein $(Z)_\beta$ is independently halogen, lower alkyl, lower alkoxy, haloalkyl, amino, nitro, cyano, carbamoyl, amido, hydroxy, cycloalkyl, lower alkenyl, lower alkynyl, or phenyl; and $\beta$ is from 0 to about 5 with the proviso that when $\beta$ is 0 that Y is piperidinylmethyl; and the pharmaceutically acceptable salts thereof, which are useful as cardiac antiarrhythmics.

BRIEF DESCRIPTION OF THE INVENTION

The compounds in accordance with the present invention are structurally generally characterized by two aromatic regions coupled through a linkage region as shown below

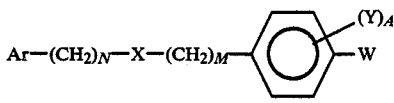

The first aromatic region

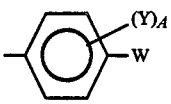

includes a para-substituted phenyl group having one or two alkyl- or arylaminomethyl substituents positioned adjacent (ortho) thereto. The para-substituent W may be hydrogen, hydroxy, amino,

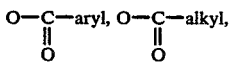

—O—alkyl, alkylsulfonamido or —O—aralkyl and A is 2; and hydroxy, amino,

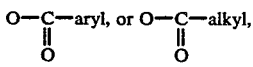

—O—alkyl, or —O—aralkyl when A is 1. Preferably W is hydroxy, amino,

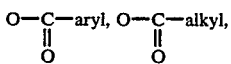

—O—alkyl, or —O—aralkyl when A is either 1 or 2. Illustrative of W subsitutents having the formula

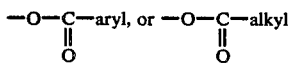

are those including but not limited to lower acyloxy groups such as acetoxy, propionyloxy, butyryloxy, and aroyloxy groups such as benzoyloxy, and the like. Illustrative of W substituents having the formula —O—alkyl or —O—aralkyl are those including but not limited to lower alkyloxy and aralkyloxy groups such as methoxy, ethoxy, propoxy, butoxy, benzyloxy, phenethyloxy, phenepropyloxy, and the like. In accordance with the present invention, we have advantageously found parahydroxy substituents effective as antiarrhythmics; thus W is most preferably hydroxy.

The alkyl or arylaminomethyl substituents of the present invention are represented by the general formula —$CH_2NR_2R_3$, where $R_2$ and $R_3$ are the same or different and may be hydrogen, lower alkyl, hydroxyalkyl such as hydroxylated straight or branched chain lower alkyl radicals, cycloalkyl, aryl, alkoxy, aralkoxy, alkoxyaryl, or heteroaryl. In the case where $R_2$ and $R_3$ are both hydrogen, it may be necessary to employ conventional blocking reagents to the amine during preparation of these compounds which are removed after the coupling of the amino substituents as set forth below. Moreover, $R_2$ and $R_3$ cannot both be alkoxy since compounds of this type would be unstable. Illustrative of alkyl- or arylaminomethyl substituents having the formula —$CH_2NR_2R_3$ are those including but not limited to those where $R_2$ and $R_3$ are methyl, ethyl, propyl, butyl, ethanol, 2-propanol, 3-propanol, butanol, methoxy, ethoxy, phenoxy, benzyloxy, cyclopentyl, cyclohexyl, cycloheptyl, phenyl, benzyl, thiophene, furan, pyrole, pyran, thiophan, pyrrolidine, piperidine, morpholine, piperazine, thiomorpholine, and thioxane. Preferred alkylaminomethyl substituents in accordance with the present invention are dimethylaminomethyl.

Alternatively, $R_2$ and $R_3$ may together with N form a 5 to 7 membered saturated or unsaturated heterocyclic group optionally including oxygen, nitrogen, or sulfur as a second heteroatom, each which may be substituted or unsubstituted. Illustrative of heterocyclic groups formed with N are those including but not limited to pyrrolidine, piperidine, morpholine, pyridine, pyrrole, piperazine, thiomorpholine, and the like. In accordance with one embodiment of the present invention, we have advantageously found alkylaminomethyl substituents where $R_2$ and $R_3$ form heterocycles with N such as pyrrolidine, piperidine, and morpholine effective as antiarrhythmics and are thus the preferred. The most preferred heterocyclic aminomethyl substituent is pyrrolidine. In accordance with the present invention, we have found that bis-aminomethyl (A=2) substituted compounds have effective antiarrhythmic activity and are most preferred.

In accordance with a preferred embodiment of the present invention, effective antiarrhythmic compounds can be made which lack a parahydroxyl substituent (W) and thus will lack in part the ability for extended conjugation of the phenol through the aryl group (Ar). We contemplate the skin discoloration associated with changrolin is due to the oxidation of the aminophenol moiety to a quinone-like structure which could result in the formation of a strong chromophore which is deposited in the skin. Thus, in accordance with one embodiment of the present invention, the W substituent should be incapable of forming such a chromophore, and is preferably hydrogen. Preferably, when W is hydrogen, the aromatic group is bis-aminomethyl (A=2).

The second region of interest for the compounds of the present invention is the aryl group (Ar) which may either be unsubstituted or substituted with various chemical substituents, and may be optionally fused with one or more aromatic groups. In accordance with the present invention, we have found that antiarrhythmic activity is lost although anticholinergic activity was maintained in the absence of the aryl (Ar) as demonstrated by the inactivity of the unsubstituted or acetyl-substituted para-aminophenol derivative.

In accordance with the present invention the aryl group may be a 5-membered heterocyclic group having sulfur, oxygen, or nitrogen as a heteroatom, or a 7-membered heterocyclic group having nitrogen as a heteroatom. In addition, these heterocyclic groups may optionally include one or more additional heteroatoms. Illustrative aryls in accordance with the present invention are those including but not limited to phenyl, cinnamoyl, thiophene, furan, pyrrole, imidazole, pyrazole, oxazole, thiazole, triazole, tetrazole, azepine, 1,2-diazepine, or 1,4-thiazepine. Preferably, the aryl is selected from the group consisting of phenyl, cinnamoyl, thiophene, furan, pyrrole, imidazole, pyrazole, oxazole, or thiazole. More preferably, the aryl is selected from the group consisting of phenyl, cinnamoyl, thiophene, furan, pyrrole, or imidazole. Most preferably, the aryl is phenyl, or thiophene.

Illustrative of fused aryls in accordance with the present invention are those including but not limited to phenyl fused with phenyl, 5-membered heterocycles such as thiophene, furan, pyrrole, pyrazole, imidazole thiazole, oxazole, or 6-membered nitrogen heterocycles such as pyridine, pyrimidine, pyridazine, pyrazine, and the like; cinnamoyl fused with phenyl, 5-membered heterocycles such as thiophene, furan, pyrrole, pyrazole, imidazole, thiazole, oxazole, or 6-membered nitrogen heterocycles such as pyridine, pyrimidine, pyridazine, pyrazine, and the like; thiophene fused with phenyl, 5-membered heterocycles such as thiophene, furan, pyrrole, or 6-membered nitrogen heterocycles such as pyridine, pyrimidine, pyrazine, pyridazine, and the like; pyrrole fused with phenyl, 5-membered heterocycles such as thiophene, furan, pyrrole, imidazole, or 6-membered nitrogen heterocycles such as pyridine, pyrimidine, pyridazine, pyrazine, and the like; imidazole fused with phenyl, 5-membered heterocycles such as furan, pyrrole, pyrazole, and 6-membered nitrogen heterocycles such as pyridine, pyridazine, pyrimidine, pyrazine, and the like; furan fused with phenyl, 5-membered heterocycles such as furan, pyrrole, thiophene or 6-membered nitrogen heterocycles such as pyridine, pyrimidine, pyridazine, and the like. Illustrative of aryls fused with more than one aromatic group include but are not limited to anthracene, phenazene, acridine, and carbazole.

In accordance with the present invention, the fused or unfused aryls may be unsubstituted, or substituted with various chemical substituents. Illustrative substituents are those including but not limited to halogen, lower alkyl, lower alkoxy, haloalkyl such as trifluoromethyl, amino, aminoalkyl such as aminomethyl and aminoethyl, alkylamino, cyano, carbamoyl, amido, hydroxy, cycloalkyl, lower alkenyl, lower alkynyl, or phenyl. Preferred substituents are halogen such as chlorine, lower alkyl such as methyl, lower alkoxy such as methoxy, and haloalkyl such as trifluoromethyl.

In accordance with a preferred embodiment of the present invention, the aryl (Ar) group is represented by the formula

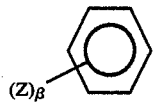

where $(Z)_\beta$ is independently halogen, lower alkyl, lower alkoxy, haloalkyl, amino, aminoalkyl, alkylamino, cyano, carbamoyl, amido, hydroxy, cycloalkyl, lower alkenyl, lower alkynyl, or phenyl. In accordance with the present invention, it is contemplated that $\beta$ may be from 0 to about 5, and preferably from 0 to 3. In accordance with one embodiment, when $\beta$ is 1 and $(Z)_\beta$ is positioned para to $-(CH_2)_N-$, $(Z)_\beta$ is halogen, lower alkoxy, haloalkyl, amino, aminoalkyl, alkylamino, nitro, cyano, carbamoyl, amido, hydroxy, cycloalkyl, lower alkenyl, lower alkynyl, or phenyl. In accordance with a further embodiment of the present invention, we have found that compounds having phenyl substituted with three methoxy groups were undesirable as antiarrhythmic agents because of the low antiarrhythmic activity associated therewith. In accordance with the present invention, we have unexpectedly and advantageously found a desirable pharmacological activities associated with compounds having a varied number of phenyl substituents and substituents at different positions. Moreover, we have found that phenyl either mono- or di-substituted ($\beta=1$ or 2) independently with halogen such as chlorine, lower alkyl such as methyl, and haloalkyl such as trifluoromethyl, provide highly effective antiarrhythmic compounds; and are thus preferred. Most preferably, the substituent or substituents are positioned ortho to $-(CH_2)_N-$, and in particular are disubstituted.

The third region of interest is the covalent linkage $-(CH_2)_N-(X)-(CH_2)_M-$ between the aromatic groups. In accordance with the present invention, this linkage has been found to tolerate modification without significant loss of pharmacological activity, and in particular antiarrhythmic potency. Linkage portions in accordance with the present invention may be those where x is

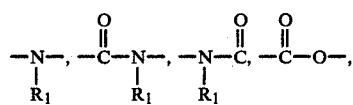

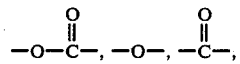

lower straight chained alkylene, or sulfur, where $R_1$ is hydrogen, lower alkyl, or aryl such as phenyl, substituted phenyl, benzyl, substituted benzyl, or heteroaryls. Preferably, x is

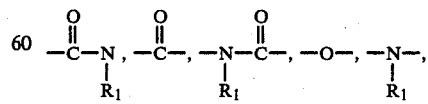

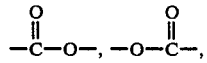

or $-O-$ where $R_1$ preferably is hydrogen or lower alkyl with hydrogen being most preferred. More preferred in accordance with the present invention are linkages where x is

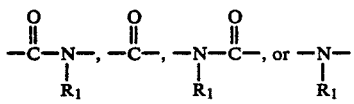

where $R_1$ is hydrogen or lower alkyl with hydrogen being most preferred. The most preferred linkages in accordance with the present invention is where x are

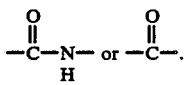

The alkylene groups in the linkage portion of these compounds may independently have from 0 to about 5 carbon atoms, and are preferably from 0 to about 2. More preferably, the linkage is such that M+N is 0, 1, or 2; and is most preferable where M+N is 0 or 1 such that M is either 0 or 1 and N is 0. Thus, illustrative linkage portions having the formula $$-(CH_2)_N-X-(CH_2)_M-$$

are those including but not limited to X, —CH₂X—, —XCH₂—, —CH₂CH₂X—, —CH₂XCH₂— —XCH₂CH₂; such as

$$-CH_2-\overset{\overset{O}{\|}}{C}-CH_2-, CH_2-\overset{\overset{O}{\|}}{C}-, -\overset{\overset{O}{\|}}{C}-, -\overset{\overset{O}{\|}}{C}-CH_2-,$$

$$-CH_2-\underset{H}{N}-\overset{\overset{O}{\|}}{C}-CH_2-, -\underset{H}{N}-\overset{\overset{O}{\|}}{C}-CH_2-, -\underset{H}{N}-\overset{\overset{O}{\|}}{C}-,$$

$$CH_2-O-CH_2, \quad -O-, \quad -CH_2O, \quad -OCH_2-,$$

$$-CH_2-\overset{\overset{O}{\|}}{C}-\underset{H}{N}-CH_2, -CH_2-\overset{\overset{O}{\|}}{C}-\underset{H}{N}-, -\overset{\overset{O}{\|}}{C}-\underset{H}{N}-, \text{ and}$$

$$-\overset{\overset{O}{\|}}{C}-\underset{H}{N}-CH_2,$$

and the like.

In accordance with one embodiment of the present invention effective antiarrhythmic compounds can be made having linkage regions which lack the ability for extended conjugation from the para-hydroxy substituent to the aryl group (Ar) as discussed above. One way of eliminating this conjugation is through the insertion of methylenes between X and the aminomethyl substituted phenolic group such that —(CH₂)ₘ— is not zero; and another way is to replace X such that extended conjugation is not possible. For example, when X is

the ability for extended conjugation is reduced.

Illustrative preferred compounds in accordance with the present invention include, but are not limited to, those represented by the list below where W is hydroxy; $(Y)_A$ is independently and preferably pyrrolidinylmethyl, piperidinylmethyl or morpholinomethyl; A is 2; $H_1$ is oxygen, nitrogen, or sulfur; Z is hydrogen or other substituent; *N a 6-membered heteroaryl containing 1 or 2 nitrogen atoms; and the aryl is bonded to the linkage portion at positions indicated by either a solid or dotted line:

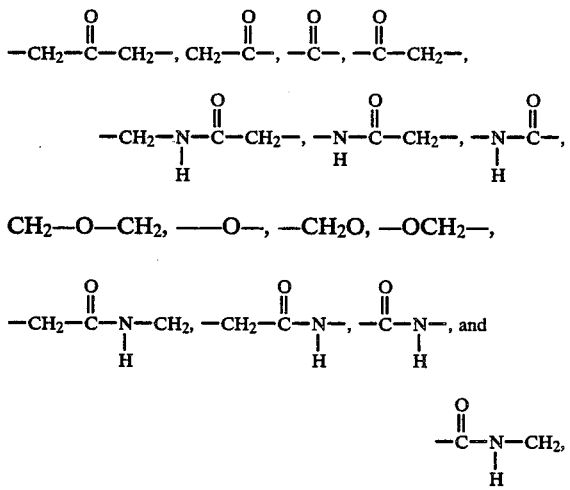

| Aryl | —(CH₂)_N | —X— | —(CH₂)_M |
|---|---|---|---|
| | N = 0 or 1 | $-\overset{\overset{O}{\|}}{C}-$ | M = 0, 1, or 2 |
| | N = 0 or 1 | $-\overset{\overset{O}{\|}}{C}-\underset{H}{N}-$ | M = 0, 1, or 2 |
| | N = 0 or 1 | $-\overset{\overset{O}{\|}}{C}-O-$ | M = 0, 1, or 2 |
| | N = 0 or 1 | $-\underset{H}{N}-$ | M = 0, 1, or 2 |
| | N = 0 or 1 | $-\underset{H}{N}-\overset{\overset{O}{\|}}{C}-$ | M = 0, 1, or 2 |
| | N = 0 or 1 | $-\overset{\overset{O}{\|}}{C}-$ | M = 0, 1, or 2 |
| | N = 0 or 1 | $-\overset{\overset{O}{\|}}{C}-O-$ | M = 0, 1, or 2 |
| | N = 0 or 1 | $-\overset{\overset{O}{\|}}{C}-\underset{H}{N}-$ | M = 0, 1, or 2 |
| | N = 0 or 1 | $-\underset{H}{N}-$ | M = 0, 1, or 2 |

-continued

| Aryl | $-(CH_2)_N$ | $-X-$ | $-(CH_2)_M$ |
|---|---|---|---|
| [indole with Z, H₁] | N = 0 or 1 | $-\overset{O}{\underset{H}{N-C}}-$ | M = 0, 1, or 2 |
| [*N(1 or 2) fused indole] | N = 0 or 1 | $-\overset{O}{C}-$ | M = 0, 1, or 2 |
| [*N(1 or 2) fused indole] | N = 0 or 1 | $-\overset{O}{C}-\overset{}{\underset{H}{N}}-$ | M = 0, 1, or 2 |
| [*N(1 or 2) fused indole] | N = 0 or 1 | $-\overset{O}{C}-O-$ | M = 0, 1, or 2 |
| [*N(1 or 2) fused indole] | N = 0 or 1 | $-\underset{H}{N}-$ | M = 0, 1, or 2 |
| [*N(1 or 2) fused indole] | N = 0 or 1 | $-\underset{H}{N}-\overset{O}{C}-$ | M = 0, 1, or 2 |
| [oxazole with H₁] | N = 0 or 1 | $-\overset{O}{C}-$ | M = 0, 1, or 2 |
| [oxazole with H₁] | N = 0 or 1 | $-\overset{O}{C}-\underset{H}{N}-$ | M = 0, 1, or 2 |
| [oxazole with H₁] | N = 0 or 1 | $-\underset{H}{N}-$ | M = 0, 1, or 2 |
| [oxazole with H₁] | N = 0 or 1 | $-\overset{O}{C}-$ | M = 0, 1, or 2 |
| [oxazole with H₁] | N = 0 or 1 | $-\underset{H}{N}-\overset{O}{C}-$ | M = 0, 1, or 2 |
| [benzoxazole with Z, H₁] | N = 0 or 1 | $-\overset{O}{C}-$ | M = 0, 1, or 2 |
| [benzoxazole with Z, H₁] | N = 0 or 1 | $-\overset{O}{C}-\underset{H}{N}-$ | M = 0, 1, or 2 |
| [benzoxazole with Z, H₁] | N = 0 or 1 | $-\overset{O}{C}-O-$ | M = 0, 1, or 2 |
| [benzoxazole with Z, H₁] | N = 0 or 1 | $-\underset{H}{N}-$ | M = 0, 1, or 2 |
| [benzoxazole with Z, H₁] | N = 0 or 1 | $-\underset{H}{N}-\overset{O}{C}-$ | M = 0, 1, or 2 |
| N*(1 or 2) [oxazole H₁] | N = 0 or 1 | $-\overset{O}{C}-$ | M = 0, 1, or 2 |
| N*(1 or 2) [oxazole H₁] | N = 0 or 1 | $-\overset{O}{C}-\underset{H}{N}-$ | M = 0, 1, or 2 |
| N*(1 or 2) [oxazole H₁] | N = 0 or 1 | $-\overset{O}{C}-O-$ | M = 0, 1, or 2 |
| N*(1 or 2) [oxazole H₁] | N = 0 or 1 | $-\underset{H}{N}-$ | M = 0, 1, or 2 |
| N*(1 or 2) [oxazole H₁] | N = 0 or 1 | $-\underset{H}{N}-\overset{O}{C}-$ | M = 0, 1, or 2 |
| [phenyl with Z] | N = 0 or 1 | $-\overset{O}{C}-$ | M = 0, 1, or 2 |
| [phenyl with Z] | N = 0 or 1 | $-\overset{O}{C}-\underset{H}{N}-$ | M = 0, 1, or 2 |
| [phenyl with Z] | N = 0 or 1 | $-\overset{O}{C}-O-$ | M = 0, 1, or 2 |

-continued

| Aryl | −(CH₂)$_N$ | −X− | −(CH₂)$_M$ |
|---|---|---|---|
|  | N = 0 or 1 | −N−<br>H | M = 0, 1, or 2 |
|  | N = 0 or 1 | $-\underset{H}{N}-\overset{O}{\underset{\|}{C}}-$ | M = 0, 1, or 2 |
|  | N = 0 or 1 | $-\overset{O}{\underset{\|}{C}}-$ | M = 0, 1, or 2 |
|  | N = 0 or 1 | $-\overset{O}{\underset{\|}{C}}-\underset{H}{N}-$ | M = 0, 1, or 2 |
|  | N = 0 or 1 | $-\overset{O}{\underset{\|}{C}}-O-$ | M = 0, 1, or 2 |
|  | N = 0 or 1 | −N−<br>H | M = 0, 1, or 2 |
|  | N = 0 or 1 | $-\underset{H}{N}-\overset{O}{\underset{\|}{C}}-$ | M = 0, 1, or 2 |
|  | N = 0 or 1 | $-\overset{O}{\underset{\|}{C}}-$ | M = 0, 1, or 2 |
|  | N = 0 or 1 | $-\overset{O}{\underset{\|}{C}}-O-$ | M = 0, 1, or 2 |

-continued

| Aryl | −(CH₂)$_N$ | −X− | −(CH₂)$_M$ |
|---|---|---|---|
| 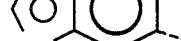 | N = 0 or 1 | $-\overset{O}{\underset{\|}{C}}-\underset{H}{N}-$ | M = 0, 1, or 2 |
| (naphthyl with *N) | N = 0 or 1 | −N−<br>H | M = 0, 1, or 2 |
| (naphthyl with *N) | N = 0 or 1 | $-\underset{H}{N}-\overset{O}{\underset{\|}{C}}-$ | M = 0, 1, or 2 |
| (indanyl H₁) | N = 0 or 1 | $-\overset{O}{\underset{\|}{C}}-$ | M = 0, 1, or 2 |
| (indanyl H₁) | N = 0 or 1 | $-\overset{O}{\underset{\|}{C}}-O-$ | M = 0, 1, or 2 |
| (indanyl H₁) | N = 0 or 1 | $-\overset{O}{\underset{\|}{C}}-\underset{H}{N}-$ | M = 0, 1, or 2 |
| (indanyl H₁) | N = 0 or 1 | −N−<br>H | M = 0, 1, or 2 |
| (indanyl H₁) | N = 0 or 1 | $-\underset{H}{N}-\overset{O}{\underset{\|}{C}}-$ | M = 0, 1, or 2 |

The compounds of the present invention and equivalents thereof possessing substantially similar pharmacological property may be prepared according to several general schemes as set forth below.

Scheme I

The arylamide derivatives of the substituted aminophenols are prepared by aminomethylation of acetominophen by the Mannich reaction, removing the acetyl group and reacting the aniline derivative with the appropriate aromatic acid chloride.

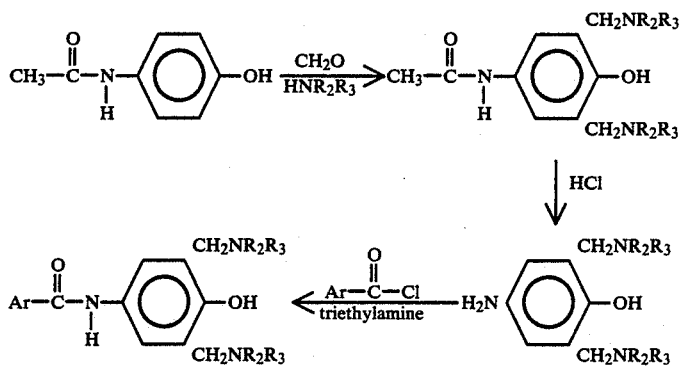

Scheme II

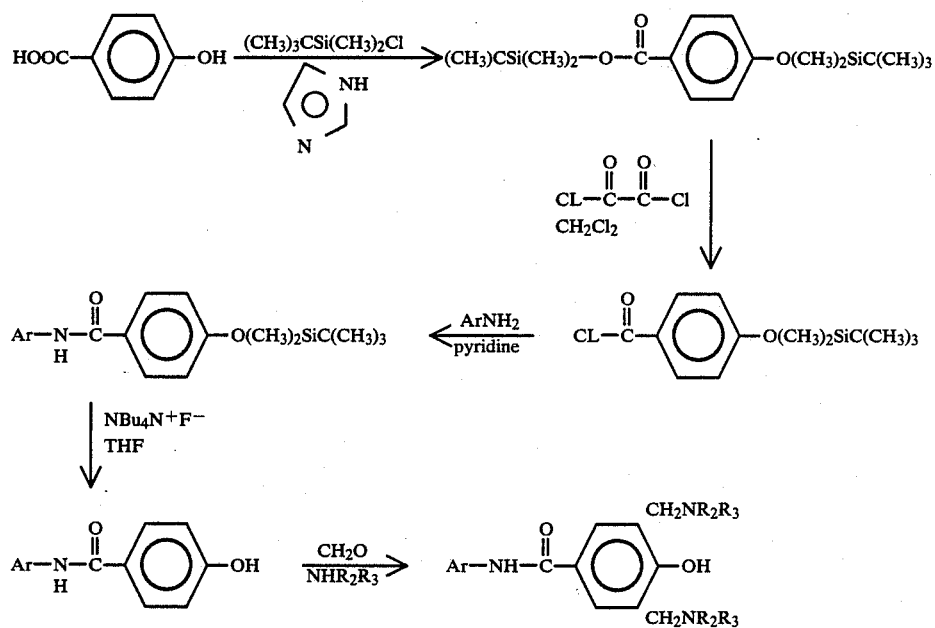

Scheme III

The aryloxy derivatives of the substituted aminophenols are prepared by aminomethylation of the appropriate p-aryloxyphenol.

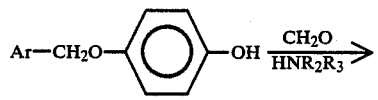

Scheme IV

The keto derivatives of the substituted phenols are prepared by aminomethylation of the appropriate p-hydroxybenzo-aryl ketone.

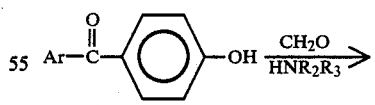

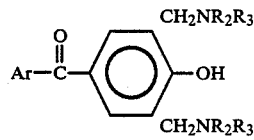

Scheme V

Aryl amide derivatives of the substituted phenols are prepared by demethylation of p-methoxybenzylamine followed by reaction with the appropriate aromatic acid chloride and aminomethylation.

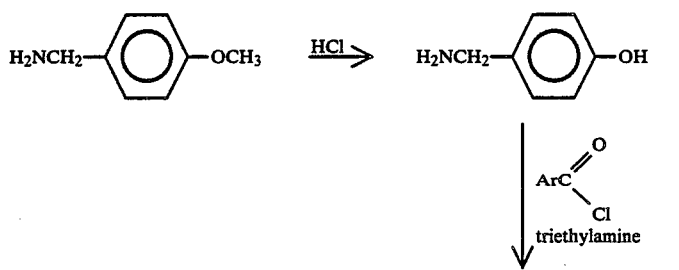
Scheme VI
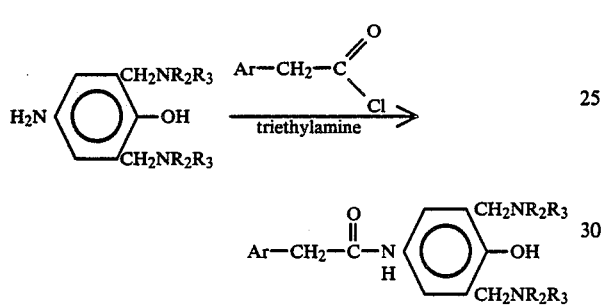
Scheme VII
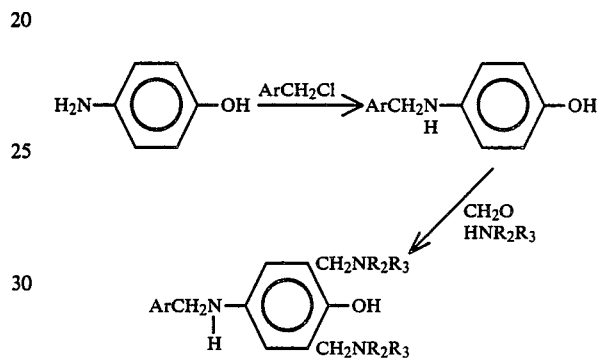
Scheme IX
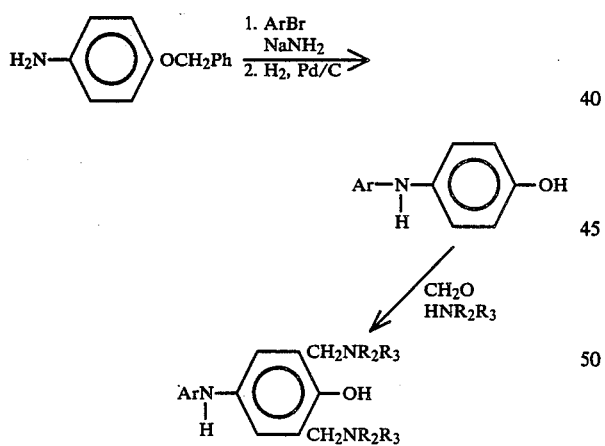
Scheme VIII
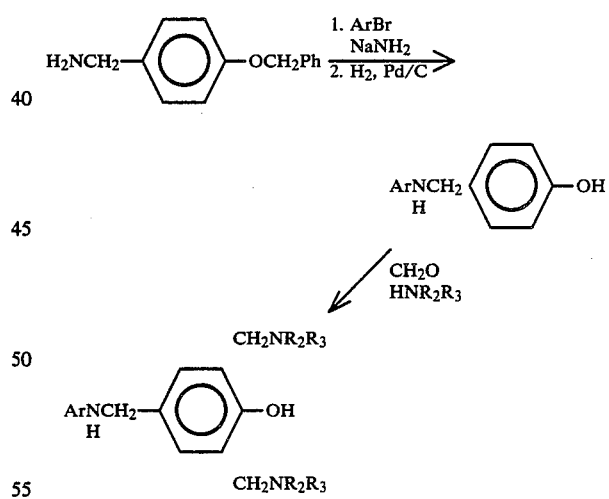
Scheme IXa
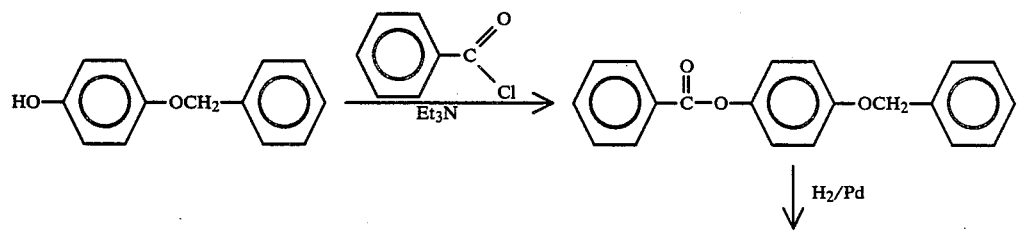

17            4,748,184            18
-continued
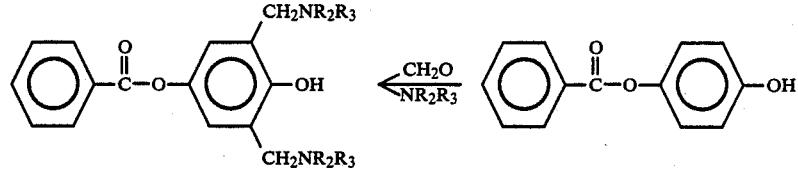
Scheme IXb
-continued
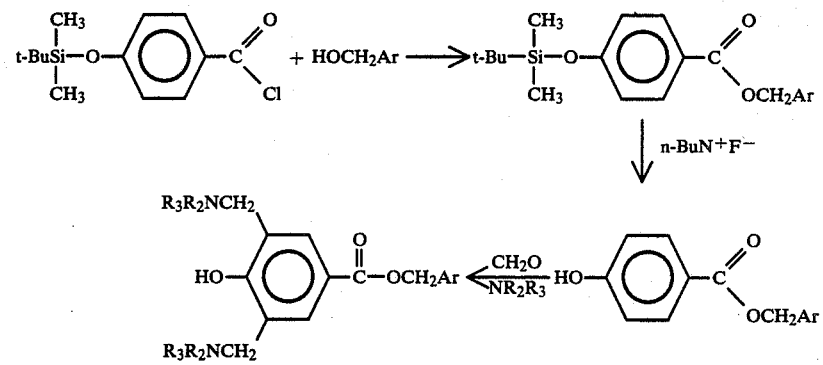
Scheme X
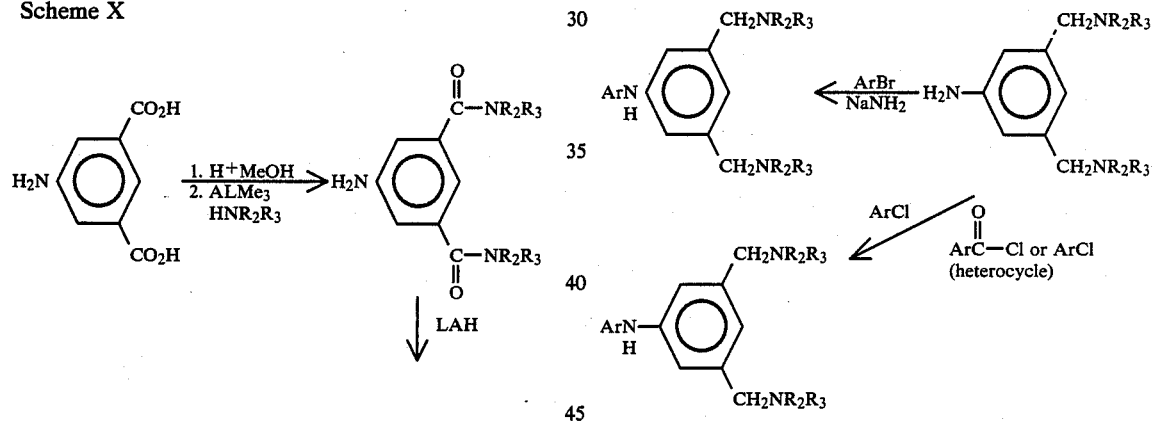
Scheme XI
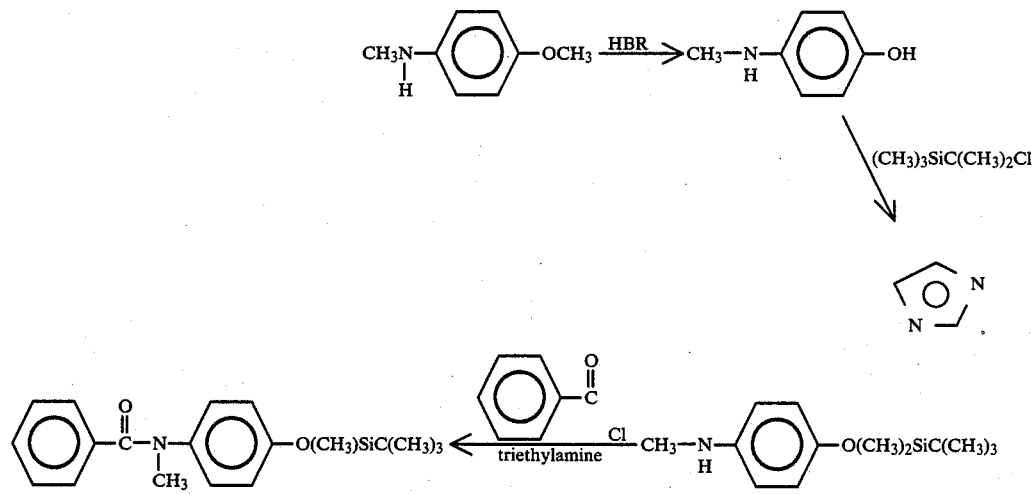

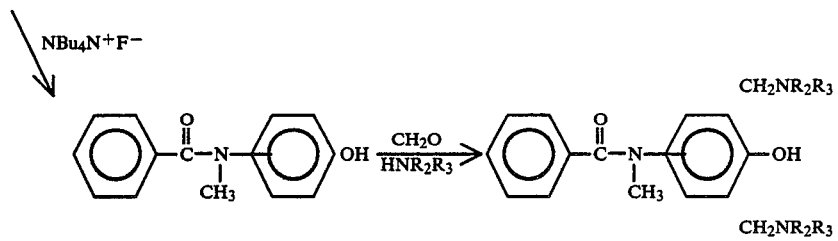

The mono-substituted aminoalkyl compounds in accordance with the present invention are co-produced with the di-substituted compounds and are separated therefrom by medium pressure liquid chromatography (MPLC) on silica gel columns.

The compounds of the present invention possess advantageous pharmacological properties useful for the treatment of cardiac arrhythmias, and in particular for the suppression of supraventricular and ventricular tachyarrthmias. It is comtemplated that these compounds, in addition to maintaining normal sinus rhythm by supression of tachyarrhythmia, will be most useful prophylactically for the prevention of premature ventricular complex formation in human patients on long-term therapy. Further, in accordance with one embodiment of the present invention, we have found that these compounds effectively suppress ventricular arrhythmias when administered orally or parenterally by infusion to dogs, while unexpectely exhibiting a benefically low anticholinergic activity in guinea pig illeum tests. These compounds also exhibit superior antiarrhythmic properties to other known antiarrhythmic agents. Thus, the desirable antiarrhythmic potency of these compounds is maximized in relationship to the undesirable side-effects associated with anticholinergic activity. Moreover, we have found a low negative inotropic activity associated with compounds in accordance with one embodiment of the present invention, which advantageously and unexpectedly reduces the incidence of a cardiodepressant effect on the heart. Compounds lacking this adverse effect on the heart would less likely cause cardiac failure. It is further contemplated that these compounds can be used as antimalarials.

The compounds in accordance with the present invention are made pharmacologically compatible, for example, by the neutralization of the free amine groups thereof with non-toxic pharmaceutically acceptable inorganic or organic salts by conventional methods. Pharmaceutically acceptable salts of these compounds are illustrated by those including but not limited to hydrochloric acid, sulfuric acid, phosphoric acid, hydrobromic acid, acetic acid, lactic acid, citric acid, oxalic acid, malic acid, salicylic acid, and the like. Further, the pharmaceutically acceptable salts of compounds in accordance with the present invention may be used in admixture with a conventional solid or liquid pharmaceutical carrier or diluent. These compositions may be administered orally or or parentally by conventional methods. For oral administration, fine powders or granules of the compound may contain diluents, binders, lubricants, and dispersing and surface active agents, and and the like may be in the dried state in coated or uncoated tablets, or in suspension. For parenteral administration, the compounds may be in aqueous injection or infusion solutions which may contain antioxidants, buffers, bacteriostats, solubilizing agents, and the like or solutes which render the salts isotonic with the blood such as in isotonic saline.

The dosage of the novel compounds of the present invention depends on several factors, as determined for conventional antiarrhythmic agents. Dosages ranging from about 1 to about 20 mg per kg of body weight were found to be effective in adult mongrel dogs (10–65 kg) when infused intravenously at a cumulative rate of 0.3 mg/kg/min. Moreover, oral dosages ranging from about 20 to about 40 mg per kg of body weight have been found effective in these doys.

The following examples are intended to be illustrative of the present invention but should not be considered as limiting the scope thereof:

EXAMPLE I 4-benzyloxy-2,6-bis(pyrrolidinylmethyl)phenol

This example describes the synthesis of a compound having the formula

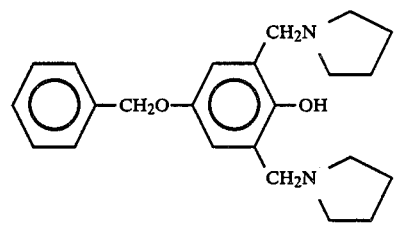

A mixture of 5 g of p-benzyloxyphenol, 6.5 ml of a 37% solution of formaldehyde, and 4.5 ml of pyrrolidone in 3 ml of ethanol was stirred with warming for 3 hours. The solvent was removed on a rotary evaporator, the product was dissolved in $CHCl_3$, the solution was washed with water, dried ($MgSO_4$) and saturated with dry hydrogen chloride affording an oil. Flash column chromatograph ($CHCl_3$/MeOH/$NH_4OH$; 9:2:0:1) again afforded an oil. The HCl salt was crystallized from i-PrOH/EtOAc, yielding white crystals: mp 139°–141° C. The IR and NMR spectra were consistent with the assigned structure and the elemental analysis was consistent with the empirical formula ($C_{23}H_{30}N_2O_2 \cdot 2HCl \cdot 0.5H_2O$).

EXAMPLE II 4-hydroxy-3,5-bis(pyrrolidinylmethyl)benzophenone

This example described the synthesis of a compound having the formula

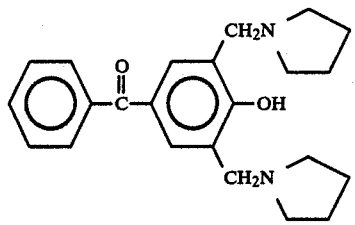

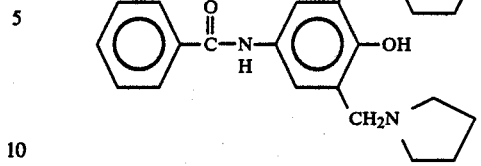

A mixture of 5 g of p-hydroxybenzophenone, 6.5 ml of a 37% solution of formaldehyde, and 4.5 ml of pyrrolidone in 3 ml of ethanol was stirred with warming for 3 hours. The solvent was removed on a rotary evaporator, the product was dissolved in $CHCl_3$, the solution was washed with water, dried ($MgSO_4$) and saturated with dry hydrogen chloride affording an oil. Flash column chromatography ($CHCl_3/MeOH/NH_4OH$; 9:2:0.05) again yielded an oil. The HCl salt was crystallized from MeOH/EtOAc giving white crystals: mp 211°–212° C. The NMR spectra were consistent with the assigned structure and the elemental analysis was consistent with the empirical formula ($C_{23}H_{28}N_2O_2.2HCl$).

EXAMPLES III–XVIII

EXAMPLE III

N-benzoyl-3,5-bis(N-pyrrolidinylmethyl)-4-hydroxyaniline

This example describes the synthesis of a compound having the formula

A mixture of 4 grams 4-acetamidophenol, 6.4 ml of a 37% solution of formaldehyde and 4.5 ml of pyrrolidone in 3 ml of ethanol was stirred with warming for 3 hours. The solvent was removed on a rotary evaporator, dissolved in $CHCl_3$, washed with water, dried ($MgSO_4$) and saturated with dry hydrogen chloride. The solvent was removed and crystallization was effected with isopropanol/ether yielding white crystals.

A solution of 100.0 g (0.315 mol) of these crystals in 200 ml of 6M HCl was heated to reflux for 3 hours. The solution was basified with solid KOH to a pH of 11. The resuling solid was collected by filtration and washed with water and cold ether. Crystallization from ether yielded pale yellow needles.

A solution having equimolar amounts of these pale yellow crystals, benzoyl chloride, and triethylamine in dioxane was stirred for 6 hours. After the solvent was removed, the products was taken up in $CHCl_3$, washed with water, dried ($MgSO_4$), and the solvent removed. The oil afforded by this procedure was purified by MPLC (EtOAc/MeOH/$NH_4OH$; 9:1:0.05) and crystallized from EtOAC: mp 160°–161° C. The IR and NMR spectra were consistent with the assigned structure and the elemental analysis was consistent with the empirical formula ($C_{23}H_{29}N_3O_2$).

The additional compounds in Table I were prepared as above with the exception that the following aroyl chlorides were substituted for benzoyl chloride. The IR and NMR spectra of each compound in Table I were consistent with the assigned structure and the elemental analysis were consistent with the empirical formulae.

TABLE I

| Example | Aroyl Chloride | M.P. (°C.) | Empirical Formula |
|---|---|---|---|
| IV | Cl-C6H4-C(O)Cl | 133–135 | $C_{23}H_{28}N_3O_2Cl$ |
| V | $H_3C$-C6H4-C(O)Cl | 50–55 | $C_{24}H_{31}N_3O_2.0.5H_2O$ |
| VI | Cl,Cl-C6H3-C(O)Cl | 118–120 | $C_{23}H_{27}N_3O_2Cl_2.2HCl.2H_2O$ |
| VII | $O_2N$-C6H4-C(O)Cl | 158–159 | $C_{23}H_{28}N_4O_4$ |

TABLE I-continued

| Example | Aroyl Chloride | M.P. (°C.) | Empirical Formula |
|---------|----------------|------------|-------------------|
| VIII | H₃CO-C₆H₄-C(=O)Cl (para-methoxy) | 55–57 | $C_{24}H_{31}N_3O_3$ |
| IX | C₆H₄(CF₃)-C(=O)Cl | 90–93 | $C_{24}H_{28}N_3O_2F_3 \cdot HCl \cdot H_2O$ |
| X | 2-Cl-C₆H₄-C(=O)Cl | 139–149 | $C_{23}H_{28}N_3O_2Cl$ |
| XI | 3-Cl-C₆H₄-C(=O)Cl | 79–83 | $C_{23}H_{28}N_3O_2Cl \cdot 2HCl \cdot H_2O$ |
| XII | 2-CF₃-C₆H₄-C(=O)Cl | 113–115 | $C_{24}H_{28}N_3O_2F_3 \cdot 2HCl \cdot 1.5H_2O$ |
| XIII | 4-F₃C-C₆H₄-C(=O)Cl | 165–166 | $C_{24}H_{28}N_3O_2F_3$ |
| XIV | 2-OCH₃-C₆H₄-C(=O)Cl | 233–235 | $C_{24}H_{31}N_3O_3 \cdot 2HCl$ |
| XV | 3-CH₃-C₆H₄-C(=O)Cl | 69 | $C_{24}H_{31}N_3O_2 \cdot 2HCl \cdot 0.125H_2O$ |
| XVI | 2-CH₃-C₆H₄-C(=O)Cl | 204–205 | $C_{24}H_{31}N_3O_2 \cdot 2HCl \cdot 1.5H_2O$ |
| XVII | 2,6-Cl₂-C₆H₃-C(=O)Cl | 185–187 | $C_{23}H_{27}N_3O_2Cl_2 \cdot 2HCl \cdot H_2O$ |

TABLE I-continued

| Example | Aroyl Chloride | M.P. (°C.) | Empirical Formula |
|---|---|---|---|
| XVIII | H3CO, H3CO, H3CO-C6H2-COCl | 70 | $C_{26}H_{35}N_3O_5$ |
| IXX | 2,6-(CH3)2-C6H3-COCl | 74–76 | $C_{25}H_{33}N_3O_2 \cdot 2HCl \cdot 3H_2O$ |
| XX | 2-thienyl-COCl | 88 | $C_{21}H_{27}N_3O_2S \cdot 0.5H_2O$ |

TABLE Ia

| Example | Compound Name |
|---|---|
| IV | N—(4-chlorobenzoyl)-3,5,-bis(N—pyrrolidinylmethyl)-4-hydroxyaniline |
| V | N—(4-methylbenzoyl)-3,5,-bis(N—pyrrolidinylmethyl)-4-hydroxyaniline |
| VI | N—(2,4,dichorobenzoyl)-3,5,-bis(N—pyrrolidinylmethyl)-4-hydroxyaniline |
| VII | N—(4-nitrobenzoyl)-3,5,-bis(N—pyrrolidinylmethyl)-4-hydroxyaniline |
| VIII | N—(4-methoxybenzoyl)-3,5,-bis(N—pyrrolidinylmethyl)-4-hydroxyaniline |
| IX | N—(3-trifluoromethylbenzoyl)-3,5,-bis(N—pyrrolidinylmethyl)-4-hydroxyaniline |
| X | N—(2-chlorobenzoyl)-3,5,-bis(N—pyrrolidinylmethyl)-4-hydroxyaniline |
| XI | N—(3-chlorobenzoyl)-3,5,-bis(N—pyrrolidinylmethyl)-4-hydroxyaniline |
| XII | N—(2-trifluoromethylbenzoyl)-3,5,-bis(N—pyrrolidinylmethyl)-4-hydroxyaniline |
| XIII | N—(4-trifluoromethylbenzoyl)-3,5,-bis(N—pyrrolidinylmethyl)-4-hydroxyaniline |
| XIV | N—(2-methoxybenzoyl)-3,5,-bis(N—pyrrolidinylmethyl)-4-hydroxyaniline |
| XV | N—(3-methylbenzoyl)-3,5,-bis(N—pyrrolidinylmethyl)-4-hydroxyaniline |
| XVI | N—(2-methylbenzoyl)-3,5,-bis(N—pyrrolidinylmethyl)-4-hydroxyaniline |
| XVII | N—(2,6,dichlorobenzoyl)-3,5,-bis(N—pyrrolidinylmethyl)-4-hydroxyaniline |
| XVIII | N—3,4,5,trimethoxybenzoyl)-3,5,-bis(N—pyrrolidinylmethyl)-4-hydroxyaniline |
| IXX | N—(2,6,dimethylbenzoyl)-3,5,-bis(N—pyrrolidinylmethyl)-4-hydroxyaniline |
| XX | N—(2-thiophenecarbonyl)-3,5-bis(N—pyrrolidinylmethyl)-4-hydroxyaniline |

EXAMPLE XXI

N-(2-thiophenemethyl)carbonyl)-3,5,bis(N-pyrrolidinylmethyl)-4-hydroxyaniline This example describes the synthesis of a compound having the formula

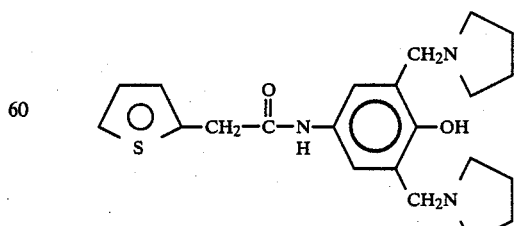

A solution having equimolar amounts of 3,5-bis(N-pyrrolidinylmethyl)-4-hydroxyaniline, 2-thiopheneacetyl chloride, and triethylamine in dioxane was stirred for 6 hours. After the solvent was removed, the product was taken up in CHCL$_3$, washed with water dried (MgSO$_4$), and the solvent removed. The oil afforded by this procedure was purified by MPLC (EtOAC/MeOH/NH$_4$OH, 9:1:0.05) and crystallized from EtOAc: mp 182° C. The IR and NMR spectra were consistent with the assigned structure and the elemental analysis was consistent with the empirical formula (C$_{22}$H$_{29}$N$_3$O$_2$S).

EXAMPLES XXII-XXVII

EXAMPLE XXII

N-(benzoyl)-3,5-bis(pyrrolidinylmethyl)-4-hydroxybenzylamine

This example describes the synthesis of a compound having the formula

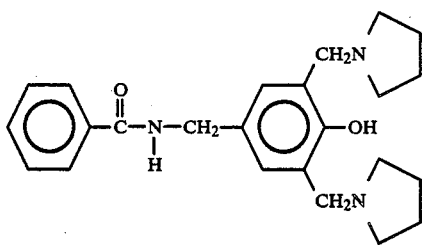

A solution having equimolar amounts of p-hydroxybenzylamine, benzoyl chloride, and triethylamine in dioxane was stirred for 6 hours. After the solvent was removed, the product was taken up in CHCl$_3$, washed with water, dried (MgSO$_4$), and the solvent was purified by MPLC and crystallized from EtOAc. The crystallized product was aminomethylated by mixing 6 g of the product, 6.5 ml of a 37% solution of formaldehyde, and 4.5 ml of pyrrolidine in 3 ml of ethanol and stirring for 3 hours with warming. The solvent was removed on a rotary evaporator, the product was dissolved in CHCl$_3$, washed with water, dried (MgSO$_4$) and saturated with dry hydrogen chloride affording an oil. The solvent was removed and crystallization was effected with isopropanol/ether, yielding off-white crystals: mp 94°-95° C. The IR and NMR spectra were consistent with the assigned structure and the elemental analysis was consistent with the empirical formula (C$_{24}$H$_{31}$N$_3$O$_2$).

The additional compounds in Table II were prepared as above with the exception that the following aroyl chlorides were substituted for benzoyl chloride. The IR and NMR spectra of each compound in Table II were consistent with the assigned structure and the elemental analyses were consistent with the empirical formulae.

TABLE II

| Aroyl Chloride | M.P. (°C.) | Empirical Formula |
|---|---|---|
| XXIII  Cl-C$_6$H$_4$-C(O)Cl | 88–90 | C$_{24}$H$_{30}$N$_3$O$_2$CL.2HCl.H$_2$O |
| XXIV  (2-CF$_3$)C$_6$H$_4$-C(O)Cl | 68 | C$_{25}$H$_{30}$N$_3$O$_2$F$_3$.2HCl.H$_2$O |

TABLE II-continued

| Aroyl Chloride | M.P. (°C.) | Empirical Formula |
|---|---|---|
| XXV  (3-CF$_3$)C$_6$H$_4$-C(O)Cl | 187–188 | C$_{25}$H$_{30}$N$_3$O$_2$F$_3$.2HCl |
| XXVI  (2-Cl)C$_6$H$_4$-C(O)Cl | 90 | C$_{24}$H$_{30}$N$_3$O$_2$Cl.2HCl.2H$_2$O |
| XXVII  (3-Cl)C$_6$H$_4$-C(O)Cl | 205–207 | C$_{24}$H$_{30}$N$_3$O$_2$Cl.21HCl |

TABLE IIa

| Example | Compound Name |
|---|---|
| XXIII | N—(4-chlorobenzoyl)-3,5-bis(pyrrolidinylmethyl)-4-hydroxybenzylamine |
| XXIV | N—(2-trifluoromethylbenzoyl)-3,5-bis(pyrrolidinylmethyl)-4-hydroxybenzylamine |
| XXV | N—(3-trifluoromethylbenzoyl)-3,5-bis(pyrrolidinylmethyl)-4-hydroxybenzylamine |
| XXVI | N—(2-chlorobenzoyl)-3,5-bis(pyrrolidinylmethyl)-4-hydroxybenzylamine |
| XXVII | N—(3-chlorobenzoyl)-3,5-bis(pyrrolidinylmethyl)-4-hydroxybenzylamine |

EXAMPLE XXVIII

N-(4-aminobenzoyl)-3,5-bis(pyrrolidinylmethyl)-4-hydroxyaniline

This example describes the synthesis of a compound having the formula

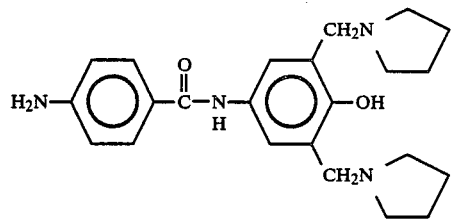

A solution having equipmolar amounts of 3,5-bis(N-pyrrolidinylmethyl)-4-hydroxyaniline, p-nitrobenzoyl chloride, and triethylamine in dioxane was stirred for 6 hours. After the solvent was removed, the product was taken up in CHCl$_3$, washed with water, dried (MgSO$_4$), and the solvent removed. The oil afforded by this procedure was purified by MPLC (EtOAc/MeOH/NH$_4$O$_4$, 9:1:0.05) and crystallized from EtOAc yielding a product having a m.p. of 158°–159° C. and an elemental analysis consistent with the empirical formula of C$_{23}$H$_{28}$N$_4$O$_4$. This product was then hydrogenated (Pd/C, EtoH) to yield the compound having a m.p. of 88°–90° C. The IR and NMR spectra were consistent with the assigned structure and the elemental analysis was consistent, with the empirical formula (C$_{23}$H$_{30}$N$_4$O$_2$).

EXAMPLE XXIX 3,5-bis(N-pyrrolidinylmethyl)-4-hydroxyacetanilide

This example describes the synthesis of a compound having the formula

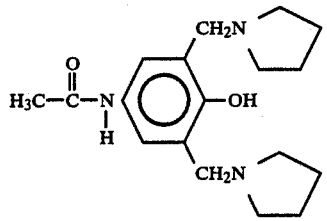

A mixture of 4 grams 4-acetamidophenol, 6.5 ml of a 37% solution of formaldehyde and 4.5 ml of pyrrolidine in 3 ml of ethanol was stirred with warming for 3 hours. The solvent was removed on a rotary evaporator, dissolved in $CHCl_3$, wased with water, dried ($MgSO_4$) and saturated with dry hydrogen chloride. The solvent was removed and crystallization was effected with isopropanol/ether yielding white crystals: mp 73°–76° C. The IR and NMR spectra were consistent with the assigned structure and the elemental analysis was consistent with the empirical formula ($C_{18}H_{27}N_3O_2.2.4HCl.0.5H_2O$).

EXAMPLE XXX 3,5-bis(N-pyrrolidinylmethyl)-4-hydroxyaniline

This example describes the synthesis of a compound having the formula

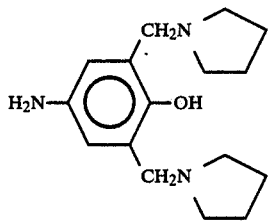

A solution of 100.0 g (0.315 mol) of the compound prepared in Example XXIX in 200 ml of 6M HCl was heated to reflux for 3 hours. The solution was basified with solid KOH to a pH of 11. The resulting solid was collected by filtration and washed with water and cold ether. Crystallization from ether yielded pale yellow needles: mp 100°–105° C. The HCl salt formed white crystals: mp 219°–221° C. The IR and NMR spectra were consistent with the assigned structure and the elemental analysis was consistent with the empirical formula ($C_{16}H_{25}N_3O$).

EXAMPLE XXXI

N-(benzoyl)3,5-bis(morpholinomethyl)-4-hydroxyaniline

This example describes the synthesis of a compound having the formula

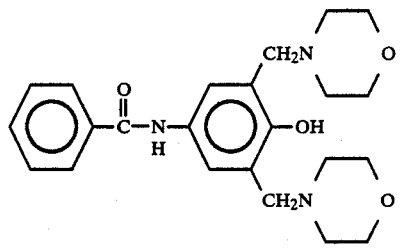

This compound was prepared as was the compound of Example III with the exception that morpholine was substituted for pyrrolidine yielding white crystals: mp 152°–154° C. The IR and NMR spectra were consistent with the assigned structure and the elemental analysis was consistent with the empirical formula ($C_{23}H_{29}N_3O_4.2.HCl.1.75H_2O$).

EXAMPLE XXXII

N-(benzoyl)3,5-bis(piperidinylmethyl)-4-hydroxyaniline

This example describes the synthesis of a compound having the formula

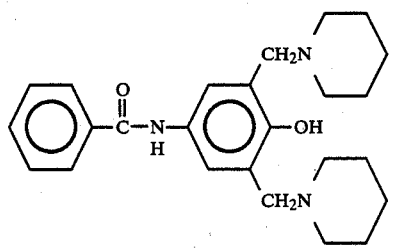

This compound was prepared as was the compound of Example III with the exception that piperidine was substituted for pyrrolidine yielding white crystals: mp 138°–140° C. The IR and spectra were consistent with the assigned structure and the elemental analysis was consistent with the empirical formula ($C_{25}H_{33}N_3O_2.2HCl.2H_2O$).

EXAMPLE XXXIII

N-([3,5-bis(pyrrolidinylmethyl)-4-hydroxy]benzoyl)aniline

This example describes the synthesis of a compound having the formula

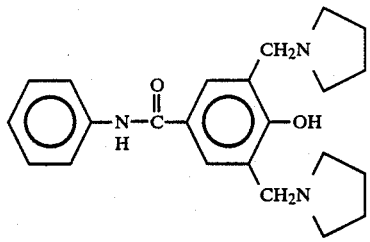

Following the method by Corey and Venkateswarlu *J. Amer. Chem. Soc* 94, 6190 (1972) for protecting alcohols and carboxylic acids, 19.7 g (0.290 mole) of imidazole was added to a solution of 10 g (0.072 mole) of p-hydroxybenzoic acid and 22.9 g (0.152 mole) of tertbutyldimethylsilylchloride in 20 ml of DMF. The solution was heated at 50°-60° C. for 5 hours, after which it was poured into H$_2$O and extracted with CH$_2$Cl$_2$. The organic phase was washed with a saturated solution of NaHCO$_3$ and dried over MgSO$_4$. The solvent was removed under reduced pressure to give a clear, colorless oil which solidified upon standing.

Upon Wissner's *J. Org. Chem.* 43, 3972 (1978) procedure for preparing carboxylic acid chloride under neutral conditions, the crude product was dissolved in 26 ml of CH$_2$Cl$_2$ containing 12 drops of DMF. The solution was cooled at 0° C. and to this was added 4.1 ml (0.049 mole) of oxalyl chloride. The solution was stirred for 1.5 hours at 0° C. and for 40 hours at room temperature. The solvent was stripped off, leaving an oil. This acid chloride was used immediately without further purification.

A solution of the crude acid chloride and 3.4 ml of (0.042 mole) of pyridine in CH$_2$Cl$_2$ was cooled to 0° C.-15° C. To this solution was added 3.2 ml (0.035 mole) of aniline, maintaining the temperature below 20° C. After stirring the solution for 2.5 hours at room temperature, the solvent was stripped off giving a mixture of orange oil and white solids. The residue was dissolved in H$_2$O and extracted with CH$_2$Cl$_2$. The combined extracts were dried over MgSO$_4$ and filtered. After stripping off the solvent under reduced pressure, an orange solid was obtained.

As described in Corey and Venkateswarlu's procedure for cleaving off the tert-butyldimethylsilyl group, the orange solid was treated with 70 ml of 1M solution of N—Bu$_4$N$^+$F$^-$ in THF (0.07 mole F$^-$) for 5 minutes at 0° C. and for 45 minutes at 25° C. After quenching the reaction with H$_2$O, the aqueous mixture was extracted with CH$_2$Cl$_2$. The CH$_2$CL$_2$ extracts were dried over MgSO$_4$ and filtered. After stripping off the solvent, 6.5 g (87%) of p-hydroxybenzanilide was obtained.

A mixture of 6.5 (0.031 mole) of the p-hydroxybenzanilide, 5.1 ml (0.067 mole) of pyrrolidine in 100 ml of ethanol was refluxed for 11 hours. After the reaction was complete, the solvent was removed on a rotary evaporator giving a yellow residual oil. Purification by medium pressure liquid chromatography on silica gel (ETOAC/MeOH/NH$_4$OH, 4:1:0.01) and recrystallization from ETOAC afforded 2.25 g (19%) of white solids: mp 154.5°-155.5° C. The HCl salt was made by dissolving 1.85 g (0.0049 mole) of the free base in CH$_2$Cl$_2$-ether and bubbling HCl gas into the solution. After removal of the solvent, 2.50 g of white solids were obtained: mp 88°-90° C. The IR and NMR spectra were consistent with the assigned structure and the elemental analysis was consistent with the empirical formula (C$_{23}$H$_{29}$N$_3$O$_2$.2HCl.1¼H$_2$O).

EXAMPLE XXXIV (N-benzoyl)-N-(methyl)-3,5-bis(pyrrolidinylmethyl)-4-hydroxyaniline This example describes the synthesis of a compound having the formula

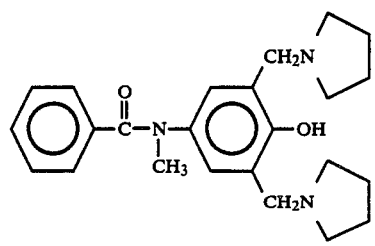

A mixture of 10 g (0.073 mole) of p-methoxyanisidine and 90 ml (0.80 mole) of HBr (48% aqueous solution) was refluxed for 6 hours. Excess HBr was removed on a rotary evaporator leaving a gray, crystalline solid residue. After neutralization with conc. NH$_4$OH, the aqueous solution was extracted and filtered. Removal of the solvent under reduced pressure afforded a solid residue.

Protection of the hydroxyl group with tert-butyldimethylsilyl group was accomplished in Example XXXIII above.

Next, to a cooled solution (−10° C. to 0° C.) of 7.0 g (0.029 mole) of the protected-phenolic product in 50 ml of dioxane was added 20.2 ml (0.145 mole) of triethylamine and 4.1 g (0.029 mole) of benzoyl chloride. The mixture was allowed to warm to room temperature and stirred for 18 hours. White precipitates of Et$_3$N.HCl were filtered off, and the filtrate was stripped off to give a dark oil which was taken up in ether and washed successively with H$_2$O, saturated NaHCO$_3$ solution and brine. The ethereal phase was dried over MgSO$_4$, and removed in a rotary evaporator to give an oily residue.

The tert-butyldimethylsilyl group was cleaved off by n—Bu$_4$N$^+$F$^-$ in THF as described in Example XXXIII.

Aminomethylation was achieved by refluxing the deprotected intermediate with 4.8 ml (0.064 mole) of formaldehyde (37% solution) and 5.3 ml (0.064 mole) of pyrrolidine in 100 ml ethanol for 11 hours. After completion of the reaction, the solvent was stripped off under reduced pressure, giving a dark oil. The oil was purified by medium-pressure liquid chromatography on silica gel (EtoAC/MeOH/NH$_4$OH, 4:1.0:0.01) to give off-white crystal solids. The HCl salt was made by dissolving the free amine in ether and bubbling HCl gas into the solution: mp 63°-65° C. The IR and NMR spectra were consistent with the assigned structure and the elemental analysis was consistent with the empirical formula (C$_{24}$H$_{31}$N$_3$O$_2$.2HCl.2¾H$_2$O).

EXAMPLE XXXV

N-(4-trifluoromethyl)-3,5-bis(pyrrolidinylmethyl)-4-hydroxybenzylamine

This example describes the synthesis of a compound having the formula

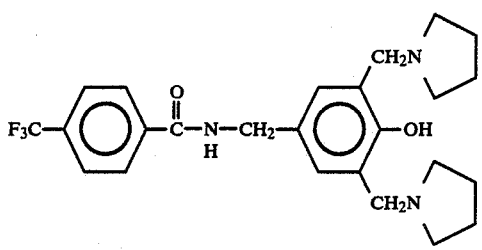

This compound was prepared as was the compound of Example XXII with the exception that 4-trifluoromethylbenzoyl chloride was substituted for benzoyl chloride yielding white crystals: mp 85°–87° C. The IR and NMR spectra were consistent with the assigned structure and the elemental analysis was consistent with the empirical formula ($C_{25}H_3ON_3O_2F_3.2HCl.H_2O$).

EXAMPLE XXXVI 2,6-bis(pyrrolidinylmethyl)-4-benzyl-phenol

This example describes the synthesis of a compound having the formula

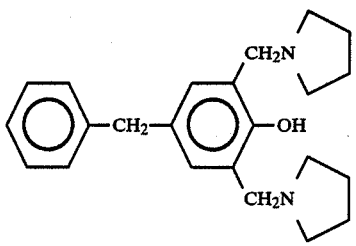

The aminomethylation of 4-hydroxydiphenylmethane was carried out as p-benzyloxyphenol of Example I affording an oil. Purification by MPLC (EtOAc/MeOH/$NH_4OH$ 4:1:0.05) on silica gel afforded a clear viscous oil. Crystallization from isopropanol yielded white crystals: mp 196°–198° C. The IR and NMR spectra were consistent with the assigned structure and the elemental analysis was consistent with the empirical formula ($C_{25}H_{28}N_5Cl$).

EXAMPLE XXXVII

The following examples describe the pharmacological evaluation of the compounds made in accordance with the present invention. In particular, these examples describe the evaluation of antiarrhythmic activity by coronary ligation in the well known Harris dog model. Ventricular arrhythmias were induced in adult mongrel dogs (10–15 kg) of either sex by two-stage ligation of the left anterior descending coronary artery. On the following day a high percentage of (90–100%) of ectopic beats existed. The test compound in saline was infused intravenously at a cumulative rate of 0.3 to 1.2 mg/kg/min (base) until normal sinus rhythm or toxicity occurred. Normal sinus rhythm was defined as 90–100% normal complexes over a 5 min period. The results of these tests are set forth in Table III.

EXAMPLE XXXVIII

The following examples describe the in vitro evaluation of anticholinergic activity in the isolated guinea pig ileum. Fasted, male Hartley guinea pigs (300–400 g) were killed by a blow to the head. A 1 cm segment of ileum was removed and placed in a bath containing physiological saline solution (in mmol/L: NaCl, 120; $NaHCO_3$, 25; KCl, 4.7; $MgSO_4$, 0.57; $KH_2PO_4$, 1.2; $CaCl_2$, 1.96; dextrose, 11.1). One end of the ileal strip was impaled onto a platinum wire electrode; and the other end was tied to a stationary glass rod. Basal tension was set at 0.1–0.3 g and peak developed tension in response to field stimulation (100–150 V, 10 msec pulse duration, 0.2 Hz) was measured with a tension transducer. Tension development was then assessed after test drug was at a concentration of 4 mg/L. Since contractile tension in this preparation is due to cholinergic activity, the percent inhibition was termed the anticholinergic activity of the drug; the greater the percent inhibition the greater the anticholinergic activity. The results of these tests are set forth in Table III.

EXAMPLE XXXIX

The following example describes the in vitro evaluation of negative inotropic activity in the cat papillary muscle. The heart of anesthetized cats (1–3 Kg) was removed through a left thoracotomy and placed into a bath containing physiological saline solution (in mmoles/L: NaCl, 128; KCl, 4.0; $NaHCO_3$, 20; $KH_2Po_4$, 1.8; $CaCl_2$, 2.5; $MgCl_2$, 0.5; dextrose 5.5) having a pH of 7.4, at room temperature. Thereafter the heart was transferred to a dissecting dish containing physiological saline at 35° C. and bubbled with 95% $O_2$/5% $CO_2$, where the atrial tissue was removed and discarded. The papillary muscle was removed from the heart after in situ measurement of its diameter; the apical and tedinous ends of the muscle were tied to the stationary glass hook of a platinum field-stimulation electrode with 4-0, 5-0, or 6-0 silk or nylon suture. The stimulating electrode and attached muscle were carefully transferred into 30 ml bath containing physiological saline at 35° C. bubble with 95% $O_2$/5% $CO_2$, pH 7.4. The suture previously tied to the tendinous end of the muscle was then attached to the outer hook of tension transducer where the muscle was gently stretched to the peak of its length-tension curve ($L_{max}$) while being stimulated by constant current pulses just above threshold intensity with a duration of 5 msec and a frequency of 0.2 Hz. The muscle was equilibrated at $L_{max}$ with just above threshold intensity pulses for 90–120 minutes. The test compound was administered at 4 mg/ml to determine the percent inhibition of tension development.

EXAMPLE XL

The following examples describe the pharmacological evaluation of the compounds in accordance with the present invention. In particular, these examples describe the evaluation of antiarrhythmic activity in the Oubain dog model. Ventricular arrhythmias were induced in dogs by intravenous administration of oubain until sustained ventricular tachycardia was present (greater than 95% ectopic beats) for 10 minutes. The test compound was infused intravenously in saline at a rate of about 0.3 to about 5 mg/kg/min until normal sinus rhythm or toxicity occurred. Normal sinus rhythm was defined as 90–100% normal complexes over a 5 minute period. The results of these tests are set forth in Table III.

TABLE III

| Compound (Example No.) | Anti-arrhythmic ED[1] in Harris Dog (mg/kg IV) | Anti-arrhythmic ED[1] in Ouabain Dog (mg/kg IV) | Anticholinergic Inhibition of Guinea Pig Ileum (% inhibition at 4 mg/L) |
|---|---|---|---|
| I | 4.5 | 1.5 | 62 |
| II | 11 | 1.9 | 9 |
| III | 5 | 3.4 | 35 |
| IV | 7 | 1.5 | 49 |
| V | 15 | 3 | 22 |
| VI | — | low activity | 11 |
| VII | — | 11 | 24 |
| VIII | — | 7.2 | 24 |
| IX | — | 2.25 | 62 |
| X | — | 5.8 | 0 |
| XI | — | 3.75 | 37 |
| XII | — | 6.2 | 0 |
| XIII | 9.0 | 5.25 | 43 |
| XIV | — | 3.0 | 31 |
| XV | — | 5.3 | 32 |
| XVI | — | 2.0 | 9.4 |
| XVII | — | 2.0 | 14.3 |
| XVIII | — | inactive[2] | 5.9 |
| IXX | — | 4.3 | 15 |
| XX | — | 1.9 | 4 |
| XXI | — | low activity | 13 |
| XXII | — | 3.0 | 32 |
| XXIII | — | 3.8 | 56 |
| XXIV | — | 1.7 | 8.5 |
| XXV | — | 5.5 | 72 |
| XXVI | — | 2.3 | 18 |
| XXVII | — | 9.8 | 78 |
| XXVIII | — | 4.5 | 0 |
| XXIX | inactive[2] | — | — |
| XXX | inactive[2] | — | 3 |
| XXXI | — | 16.5 | 37 |
| XXXII | — | 11 | 33 |
| XXXIII | — | 3.5 | — |
| XXXIV | — | 16 | 16 |
| XXXV | — | 4.5 | 49 |
| XXXVI | low activity | — | 14 |
| Quinidine | 10.1 | — | 62 |
| Disopyramide | 6.8 | 4.4 | 81 |
| Changrolin | 10.3 | 5.5 | 43 |

[1] ED is the effective dose required to sustain normal sinus rhythm.
[2] No effect on sinus rhythm up to a cumulative dose of 30 mg per kg.

EXAMPLE XLI

The compounds listed in Table IV were prepared by one of the three different methods described. The method employed for individual compounds is designated in Table IV.

Synthetic Method A

Due to the commercial availability of the appropriate 4-hydroxybenzoates, compounds, 1, 2–15, 24, 26 and 27 were prepared in one step. A typical example is the aminomethylation of methyl 4-hydroxybenzoate to yield compound 1.

To a solution of 0.10–0.14 moles of methyl 4-hydroxybenzoate was added, in one lot, a combination of 0.22–0.31 moles pyrrolidine and 0.30–0.42 moles 37% aqueous formaldehyde solution which was premixed at ice-bath temperature. This reaction mixture was stirred at reflux for 16–20 hours. The mixture was concentrated under reduced pressure to afford an oil which was partitioned between water and ethyl acetate. The organic layer was dried ($MgSO_4$) and filtered. This filtrate was concentrated under reduced pressure to give an oil which was dissolved in ether and treated with HCL(g) until acidic. The precipitated dihydrochloride salt was collected by filtration and crystallized from methanol/ether.

Synthetic Method B

Compounds 16–22 was prepared by reacting a volatile, acid-stable alcohol with the appropriate carboxylic acid and HCl as described below for compound 17.

A solution of 0.08–0.12 moles of 3-(4'-hydroxyphenyl)propanoic acid in 300–500 ml of ethanol was saturated with HCl(g). This mixture was stirred at reflux for 16–20 hours. Volatiles were removed under reduced pressure to yield the product oil, ethyl 3-(4'-hydrroxyphenyl)propanoate.

The ester obtained was reacted with pyrrolidine and formaldehyde as described in Synthetic Method A to yield compound 17.

Synthetic Method C

Esters of non-volatile or acid-unstable alcohols were prepared in a manner analogous to that described below for compound 25.

A suspension of 7.0–7.4 moles 4-hydroxybenzoic acid in 18.8–19.2 moles of acetic anhydride is stirred over a steam bath. On addition of a catalytic amount (0.5–1.5 ml) of concentrated sulfuric acid rapid dissolution of the 4-hydroxybenzoic acid occurred and was followed immediately by precipitation of product. This mixture was warmed by the steam bath an additional 30–60 minutes then cooled to room temperature. The slurry obtained was filtered and the filter cake was washed with water. The white solid obtained in this manner was 4-acetoxybenzoic acid and was used without further purification.

A mixture of the above product and thionyl chloride (1:6 ratio) was stirred at reflux for 16–18 hours. All volatiles were then removed under reduced pressure to give 4-acetoxybenzoyl chloride, a beige solid which was used without further purification.

To a stirred solution of 0.2–0.3 moles of acid chloride in 40–50 ml of $CHCl_3$ was added 0.2–0.3 moles of cyclohexylmethanol. The reaction mixture was stirred at reflux for 16–20 hours. Volatiles were removed under reduced pressure to give an oil which was treated with hexanes. Any insoluble material was removed by filtration and the filtrate was concentrated to give the oil, cyclohexylmethyl 4-acetoxybenzoate.

The above oil was dissolved in methanol and treated with HCL(g) for 5–10 minutes. After removal of volatiles, the remaining oil, cyclohexylmethyl 4-hydroxybenzoate was converted to compound 27 in a fashion analogous to that described in Synthetic Method A.

TABLE IV

[Structure: benzene ring with R substituent, OH, and two CH₂N-pyrrolidinyl groups]

| Compound | R | Synthetic Method | IN VITRO[a] # Tissues Converted | IN VITRO[a] Mean E.D. (μg/mL) | IN VIVO[b] Mean E.D. Bolus Ins. (MPK) | Duration of Action-Recovery Time (Minutes) 50% | 80% | 100% |
|---|---|---|---|---|---|---|---|---|
| 1 | $CH_3O_2C$ | A | 2/6 | 23.00 | 2.5 | | | |
| 2 | $HO_2C$ | A | 0/7 | — | N.C. | | | |
| 3 | $CH_3CH_2O_2C$ | A | 7/7 | 23.00 | 2.5 | | | |
| 4 | $PhO_2C$ | A | — | — | N.C. | | | |
| 5 | $(CH_3)_2CHO_2C$ | A | 3/3 | 11.43 | | | | |
| 6 | $CH_3(CH_2)_2O_2C$ | A | 3/3 | 6.60 | | | | |
| 7 | $CH_3CH_2CH(CH_3)O_2C$ | A | 2/2 | 6.70 | | | | |
| 8 | $CH_3(CH_2)_6O_2C$ | A | 2/2 | 2.00 | | | | |
| 9 | $CH_3(CH_2)_7O_2C$ | A | 1/3 | 5.00 | | | | |
| 10 | $(CH_3)_2CHCH_2O_2C$ | A | 5/5 | 3.80 | 1.75 | 5 | 20 | 45 |
| 11 | $CH_3(CH_2)_3O_2C$ | A | 3/3 | 2.30 | | | | |
| 12 | $CH_3(CH_2)_5O_2C$ | A | 3/4 | 3.46 | | | | |
| 13 | $CH_3(CH_2)_4O_2C$ | A | 2/2 | 3.50 | | | | |
| 14 | $PhCH_2O_2C$ | A | 3/5 | 2.40 | | | | |
| 15 | $CH_3(CH_2)_8O_2C$ | A | 2/6 | 3.00 | | | | |
| 16 | $CH_3CH_2O_2CCH_2$ | B | 3/3 | 16.50 | | | | |
| 17 | $CH_3CH_2O_2CCH_2CH_2$ | B | 3/3 | 15.90 | | | | |
| 18 | $CH_3O_2CCH_2CH_2$ | B | 4/4 | 23.00 | | | | |
| 19 | $FCH_2CH_2O_2C$ | B | 2/3 | 21.00 | | | | |
| 20 | $CH_3O_2CCH\overset{t}{=}CH$ | B | 4/4 | 71.20 | 30.0 | | | |
| 21 | $CH_3O_2CCH_2$ | B | 1/4 | 93.50 | | | | |
| 22 | $CH_2=CHCH_2$ | B | 3/4 | 2.67 | | | | |
| 23 | $(CH_3)_2CHCH_2NHCO$ | A | 2/4 | 12.40 | | | | |
| 24 | $CH_3(CH_2)_{11}O_2C$ | C | 2/5 | 3.00 | | | | |
| 25 | [thiophene]-$CH_2O_2C$ | C | 4/5 | 1.33 | | | | |
| 26 | $(CH_3)_2CHCH_2CH_2O_2C$ | A | 5/5 | .88 | | | | |
| 27 | $CH_3(CH_2)_3CHCH_2O_2C$ with $CH_2CH_3$ branch | A | 2/5 | 1.50 | | | | |
| 28 | [cyclopropyl]-$CH_2O_2C$ | C | 3/4 | 17.20 | | | | |

NOTES
[a] IN VITRO studies involved acetylstrophanthidin-induced arrhythmias in Guinea Pig right atria.
[b] IN VIVO studies involved Quabain dog model. Duration of action based on monitoring prolongation of QRS.
N.C. — no conversion The following test procedure was used to assess antiarrhythmic activity since the contractions elicited by the SA node of the guinea pig right atrium can be made arrhythmic by the means of an acetylstrophanthidin-induced arrhythmia with the accepted arrhythmogenic concentration (30 λ of 5 mg/ml stock in a 30 ml organ bath). Conversion of the arrhythmia with incremental doses will give an effective dose (ED) which can be used to rank the activity of these compounds. The procedure is a modification of the procedures described by R. G. Burney et al., American Heart Journal, Vol. 88, No. 6, 765(1974) and M. J. Peach et al., Journal of Pharmacol. Exp. Therapeutics, Vol. 183, 73(1972), the primary difference being that in the present procedure, an arrhythmia is created and then reversed whereas in the published procedures, the tissue is pretreated with antiarrhythmic and then an attempt is made to induce an arrhythmia.

The guinea pig's right atria is isolated and a platinum hook and gold chain are attached to the shoulder part of the atria while a stationary glass rod and hook are attached at the apex. One hour of equilibration is allowed with a wash every 20 minutes.

Acetylstophanthidin is administered (30 λ of a stock 5 mg/ml in absolute 100% ethanol) and the atria is set aside for one hour to allow arrhythmia to develop. Once sustained arrhythmia is present, an antiarrhythmic drug may be screened in incremental doses at predetermined times.

After an arrhythmia is converted to normal sinus rhythm (NSR), it should be noted that the cumulative dose is the ED.

The present invention has been described in detail and with particular reference to the preferred embodiments; however, it will be understood by one having ordinary skill in the art that changes can be made thereto without departing from the spirit and scope thereof.

What is claimed is:

1. A compound of the formula

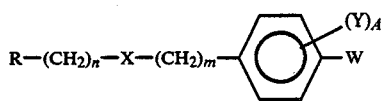

wherein X is

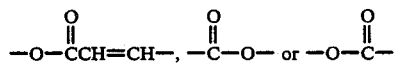

wherein W is hydrogen or hydroxy; $(Y)_A$ is positioned ortho to W and is an aminoloweralkyl having the formula —$CH_2NR_2R_3$ where $R_2$ and $R_3$ may together with N form a pyrrolidine, piperidine or azepine ring, and A is 2; n and m are independently from 0 to 5; and R is straight or branched $C_1$–$C_{10}$ alkyl, straight or branched $C_3$–$C_{10}$ cycloalkyl, straight or branched $C_2$–$C_4$ alkenyl, or straight or branched $C_2$–$C_4$ alkynyl, or a pharmaceutically acceptable salt thereof.

2. A compound of the formula

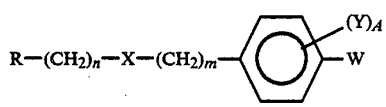

wherein X is

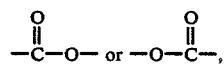

W is hydroxy, $(Y)_A$ is positioned ortho to W and is an aminoloweralkyl having the formula —$CH_2NR_2R_3$ where $R_2$ and $R_3$ together with N form a pyrrolidine or piperidine ring, n and m are each 0 to 5, and R is a straight or branched $C_1$–$C_6$ alkyl, or a pharmaceutically acceptable salt thereof.

3. A compound of claim 2 wherein $R_1$ and $R_3$ together with N form a pyrrolidine ring.

4. A compound of claim 3 wherein X is

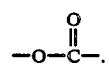

5. A compound of claim 4 wherein n is 0, 1 or 2, m is 2, and R is methyl, ethyl or cyclopropyl.

6. A compound of claim 5 wherein n is 1, m is 0, and R is cyclopropyl.

7. A compound of claim 5 wherein n is 1, m is 2, and R is methyl.

8. A compound of claim 5 wherein n is 0, m is 2, and R is methyl.

9. A cardiac arrhythmic composition containing an antiarrhythmic-effective amount of the compound having the formula

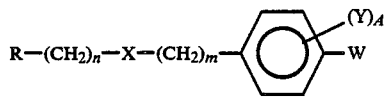

wherein X is

wherein W is hydrogen or hydroxy; $(Y)_A$ is positioned ortho to W and is an aminoalkyl having the formula —$CH_2NR_2R_3$ wherein $R_2$ and $R_3$ may together with N form a pyrrolidine, piperidine or azepine ring, and A is 2; n and m are independently from 0 to 5; and R is straight or branched $C_1$–$C_{10}$ alkyl, straight or branched $C_3$–$C_{10}$ cycloalkyl, straight or branched $C_2$–$C_4$ alkenyl, straight or branched $C_2$–$C_4$ alkynyl, or a pharmaceutically acceptable salt thereof; in admixture with a pharmaceutically acceptable carrier or diluent.

10. A cardiac arrhythmic composition containing an antiarrhythmic effective amount of the compound having the formula

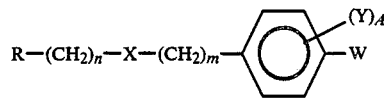

wherein X is

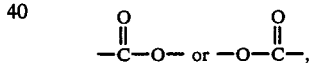

W is hydroxy, $(Y)_A$ is positioned ortho to W and is an aminoloweralkyl having the formula —$CH_2NR_2R_3$ where $R_2$ and $R_3$ together with N form a pyrrolidine or piperidine ring, n and m are each 0 to 5, and R is a straight or branched $C_1$–$C_6$ alkyl, or a pharmaceutically acceptable salt thereof.

11. The composition of claim 10 wherein $R_1$ and $R_3$ together with N form a pyrrolidine ring.

12. The composition of claim 11 wherein X is

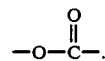

13. The composition of claim 4 wherein n is 0, 1 or 2, m is 2, and R is methyl, ethyl or cyclopropyl.

14. A method of treating cardiac arrhythmias in a patient by administration of an antiarrhythmic effective amount to such patient of a compound of the formula

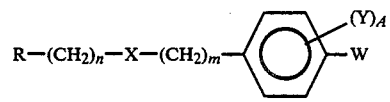

wherein X is

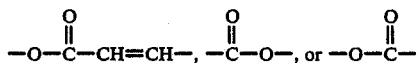

wherein W is hydrogen or hydroxy; $(Y)_A$ is positioned ortho to W and is an aminoloweralkyl having the formula $-CH_2NR_2R_3$ where $R_2$ and $R_3$ may together with N form a pyrrolidine, piperidine or azepine ring, and A is 2; n and m are independently from 0 to 5; and R is straight or branched $C_1-C_{10}$ alkyl, straight or branched $C_3-C_{10}$ cycloalkyl, straight or branched $C_2-C_4$ alkynyl, or a pharmaceutically acceptable salt thereof.

15. A method of treating cardiac arrhythmias in a patient by administration of an antiarrhythmic effective amount of such patient of a compound of the formula

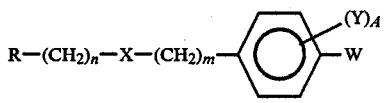

wherein X is

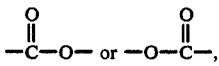

$(Y)_A$ is positioned ortho to W and is an aminoloweralkyl having the formula $-CH_2NR_2R_3$ where W is hydroxy, $R_2$ and $R_3$ together with N form a pyrrolidine or piperidine ring, n and m are each 0 to 5, and R is a straight or branched $C_1-C_6$ alkyl, or a pharmaceutically acceptable salt thereof.

16. The method of claim 15 wherein $R_1$ and $R_3$ together with N form a pyrrolidine ring.

17. The method of claim 16 wherein X is

18. The method of claim 17 wherein n is 0, 1 or 2, m is 2, and R is methyl, ethyl or cyclopropyl.

19. The method of claim 18 wherein n is 1, m is 0, and R is cyclopropyl.

* * * * *